United States Patent
Ben Hamouda et al.

(10) Patent No.: US 11,988,624 B2
(45) Date of Patent: May 21, 2024

(54) METHOD FOR DETECTING AT LEAST ONE GAS QUANTITY OF AT LEAST ONE PREDETERMINED GAS BY A MEASUREMENT SENSOR OF A PLURALITY OF GASES

(71) Applicants: RUBIX S&I, Toulouse (FR); CIDEV EURL, Toulouse (FR)

(72) Inventors: Franck Ben Hamouda, Toulouse (FR); Jean-Christophe Mifsud, Goudourville (FR)

(73) Assignee: ELLONA, Toulouse (FR)

( * ) Notice: Subject to any disclaimer, the term of this patent is extended or adjusted under 35 U.S.C. 154(b) by 382 days.

(21) Appl. No.: 17/294,242

(22) PCT Filed: Nov. 22, 2019

(86) PCT No.: PCT/EP2019/082209
§ 371 (c)(1),
(2) Date: May 14, 2021

(87) PCT Pub. No.: WO2020/109160
PCT Pub. Date: Jun. 4, 2020

(65) Prior Publication Data
US 2022/0003702 A1    Jan. 6, 2022

(30) Foreign Application Priority Data

Nov. 28, 2018 (FR) .................................... 1871971

(51) Int. Cl.
*G01N 27/02* (2006.01)
*G01N 33/00* (2006.01)

(52) U.S. Cl.
CPC ......... *G01N 27/02* (2013.01); *G01N 33/0027* (2013.01)

(58) Field of Classification Search
CPC ..... G01N 27/02; G01N 27/125; G01N 27/149
(Continued)

(56) References Cited

U.S. PATENT DOCUMENTS 5,621,162 A * 4/1997 Yun ...................... G01N 27/125
                                                                    73/31.06
5,889,198 A    3/1999 Reitmeier et al.
(Continued)

FOREIGN PATENT DOCUMENTS

DE         19639072 A1    3/1998
WO    WO 2006/057550 A1    6/2006

OTHER PUBLICATIONS

Search Report from the French Intellectual Property Office on corresponding FR application (FR1871971) dated Oct. 14, 2019.
(Continued)

*Primary Examiner* — Vincent Q Nguyen
(74) *Attorney, Agent, or Firm* — Alumen IP Law PC

(57) ABSTRACT

A method for detecting a gas quantity of a predetermined gas by a sensor having a sensitive layer configured to measure a plurality of gases, having an impedance Zs and a heating layer, the method include a step of supplying the heating layer with a voltage ramp defining a linear change in the supply voltage between a low voltage value and a high voltage value to modify the temperature of the sensitive layer during a variation period, a step of measuring variations in the impedance of the sensitive layer at a plurality of temperatures of the sensitive layer during the variation period, so as to detect a plurality of gas quantities, and a step of comparing a variation of the impedance at a given temperature of the sensitive layer to associate the gas quantity measured with a predetermined gas.

7 Claims, 3 Drawing Sheets

(58) Field of Classification Search
USPC .............................. 324/465, 71.1, 464, 468
See application file for complete search history.

(56) References Cited

U.S. PATENT DOCUMENTS

| | | | | |
|---|---|---|---|---|
| 6,083,370 | A * | 7/2000 | Kato | G01N 27/4065 |
| | | | | 204/425 |
| 6,120,663 | A * | 9/2000 | Kato | G01N 27/419 |
| | | | | 204/425 |
| 2019/0310216 | A1* | 10/2019 | Shim | G01N 27/125 |
| 2020/0278310 | A1* | 9/2020 | Ninos | G01N 27/124 |

OTHER PUBLICATIONS

International Search Report and Written Opinion on corresponding PCT application (PCT/EP2019/082209) from International Searching Authority (EPO) dated Jan. 31, 2020.

Kohler H et al.: "New applications of tin oxide gas sensors—I. Molecular identification by cyclic variation of the working temperature and numerical analysis of the signals", Sensors and Actuators B: Chemical, Elsevier BV, NL, vol. 61, No. 1-3, Dec. 14, 1999, pp. 163-169.

* cited by examiner

METHOD FOR DETECTING AT LEAST ONE GAS QUANTITY OF AT LEAST ONE PREDETERMINED GAS BY A MEASUREMENT SENSOR OF A PLURALITY OF GASES

TECHNICAL FIELD

The present invention relates to the field of gas sensors and is directed more particularly to a method for controlling a gas sensor.

BACKGROUND

Today, it is common to use a sensor to measure different gases, especially in a person's breath in order to measure the blood alcohol level, inside a building in order to determine the air quality, etc.

To carry out such measurements, it is known a metal-oxide sensor, also called MOX sensor, which has a limited cost and overall size. Such an MOX sensor comprises a sensitive layer the conductivity of which varies in the presence of some gases and a heating layer on which the sensitive layer is mounted. The heating layer is supplied with electric energy by a direct voltage in order to heat the sensitive layer.

When a gas the amount of which is desired to be measured comes into contact with the sensitive layer, oxidation-reduction reactions are caused, varying the characteristics of the sensitive layer, especially its resistance, which is measured in order to detect such a variation and thus determine the amount of gas. The amount of gas allows a gas to be quantified but also its presence to be detected.

In practice, such a sensor is not efficient to detect a plurality of gases. One solution consists in multiplying the heterogeneous gas sensors in order to improve detection. Nevertheless, such a solution has the drawback of significantly increasing the detection cost.

Another solution consists in varying parameters of a single gas sensor in order to make it sensitive to several gases with different natures. Therefore, it has been provided to supply the heating layer with a stepwise varying voltage. This makes it possible to vary the temperature of the sensitive layer so that it measures different gases. However, as the number of measurements is limited, it is not possible to discriminate a large number of gases. Moreover, as the sensor is supplied by a direct voltage, its lifetime is limited.

Besides, it has been provided to apply a PWM type modulation square-wave signal in order to vary the supply voltage of the heating layer. Although this solution allows a greater number of measurements to be made, the measurements made are sensitive to variations in outdoor temperature and humidity. Also, the repeatability of the measurements is not guaranteed when the outdoor conditions vary. Moreover, the control by a PWM signal depends on the intrinsic characteristics of the sensor which vary from one sensor to another, which is further detrimental to the repeatability of the measurements.

It is also known from the paper published by Kohler H et al under the title "New applications of tin oxide gas sensors—I. Molecular identification by cyclic variation of the working temperature and numerical analysis of the signals" and the corresponding patent application DE19639072A1, a method and a system for molecular identification by cyclic variation in the temperature of a semiconductor sensor over a period of time. During a calibration phase, the sensor is successively placed in known media comprising known solvents with known concentrations and measures for each of them a conductance profile over the entire period. During an identification phase, the sensor is placed in an unknown medium comprising one or more of the known solvents from the calibration phase and measures a conductance profile over the entire period. By comparing the conductance profile of the complete unknown medium with the conductance profiles of the complete known media, an estimate of the relative concentration of each known substance in the unknown medium is determined.

From patent application U.S. Pat. No. 5,889,198A1, it is also known a method and system for detecting methane by means of a gallium oxide semiconductor sensor. The method consists in measuring a first conductance at a first temperature and then a second conductance at a second temperature different from the first temperature, obtained by heating the sensor with a linear voltage ramp. The second conductance combined with the ratio of the second conductance to the first conductance enables the associated methane concentration to be determined by comparison with a data table.

Incidentally, a method and system for detecting pollutants in the air, especially in a vehicle ventilation system, is known from patent application WO2006057550A1, which makes it possible to stop the outdoor air flow when the outdoor level of pollution is too high. The detection system comprises an electrochemical sensor comprising a sensitive layer comprising electrodes and an element heating the sensitive layer according to a temperature profile comprising an increasing and then decreasing ramp. The detection system is first placed in one or more calibration environments comprising known gases at a known concentration in order to measure and store responses to the temperature profile. The detection system is then placed in an environment comprising known gases at an unknown concentration. The response to the temperature profile is compared to the stored responses to determine the concentration of these known gases.

Thus, there is a need for a method for controlling a sensor to address at least some of these drawbacks.

SUMMARY

To this end, the invention relates to a method for detecting at least one amount of at least one predetermined gas from a sensor for measuring a plurality of gases, said sensor comprising a sensitive layer configured to measure the plurality of gases having an impedance $Z_s$ and a heating layer on which the sensitive layer is mounted, said heating layer being configured to be supplied with electric energy in order to vary the temperature of the sensitive layer, said method comprising:
 a step of supplying the heating layer with at least one voltage ramp defining a linear variation in the supply voltage between a low voltage value and a high voltage value in order to modify the temperature of the sensitive layer during a variation period,
 a step of measuring variations in the impedance $Z_s$ of the sensitive layer at several temperatures of the sensitive layer during the variation period so as to detect a plurality of gas amounts,
 a step of comparing, to a database, at least one variation in the impedance $Z_s$ of the sensitive layer measured at a given temperature of the sensitive layer, in order to associate the measured amount of gas with a predetermined gas.

The invention more precisely relates to a method for detecting at least one amount of gas of at least one predetermined gas from a sensor for measuring a plurality of gases, said sensor comprising a sensitive layer configured to measure the plurality of gases having an impedance Zs and a heating layer on which the sensitive layer is mounted, said heating layer being configured to be supplied with electric energy in order to vary the temperature of the sensitive layer, said method comprising:

a step of supplying the heating layer with at least one first increasing voltage ramp defining a linear variation in the supply voltage and then with a second decreasing voltage ramp defining a linear variation in the supply voltage between a low voltage value and a high voltage value in order to modify the temperature of the sensitive layer during a variation period according to a temperature ramp comprising an increasing portion and a decreasing portion, the temperature ramp comprising a plurality of temperature ranges $\Delta T$ each corresponding to a gas to be measured, a step of measuring:
  a first variation in the impedance Zs of the sensitive layer at a given temperature range $\Delta T$ of the sensitive layer during the first increasing ramp and
  a second variation in the impedance Zs of the sensitive layer measured at the same given temperature range $\Delta T$ of the sensitive layer during the second decreasing ramp, the temperature range $\Delta T$ corresponding to a given gas to be measured;

a step of comparing, to a database, the first variation in the impedance Zs and the second variation in the impedance Zs in order to determine the amount of gas associated with said given gas.

By virtue of the method according to the invention, it is possible to measure different gases with the measurement sensor by virtue of the temperature modification of the sensitive layer which makes it sensitive to different gases. Moreover, by virtue of the supply of the heating layer by a ramp, the temperature of the sensitive layer varies linearly and accurately. The detection of a variation associated with a temperature of the sensitive layer allows the measured amount of gas to be associated with a predetermined gas accurately and reliably. The amount of gas allows a gas to be quantified but also its presence to be detected. In other words, the method according to the invention makes it possible to determine the presence of a gas solely from the detection of a variation in impedance during the first increasing ramp and during the second decreasing ramp. The temperature range $\Delta T$ at which the variation in impedance is measured is reduced, identical for the first increasing ramp and the second decreasing ramp and characteristic of a given gas. The temperature range $\Delta T$ thus makes it possible to determine the nature of the gas and the amplitude of the variation in impedance makes it possible to determine the amount of said gas. Thus, when a gas induces a different variation in impedance Zs for an increasing ramp or a decreasing ramp, its amount can be determined more precisely by analyzing the variations in impedance.

Preferably, during the variation period, as the heating layer is supplied by a first increasing ramp and then by a second decreasing ramp, a first variation in the impedance Zs of the sensitive layer, measured at a given temperature of the sensitive layer during the first increasing ramp, and a second variation in the impedance Zs of the sensitive layer, measured at a given temperature of the sensitive layer during the second decreasing ramp, are compared to the database in order to associate the measured amounts of gas to a predetermined gas.

Thus, several variations in the impedance Zs of the sensitive layer can be measured twice at a same temperature: during the first ramp and during the second ramp. Advantageously, the behavior of the sensitive layer can be different depending on whether the temperature increases or decreases, which improves the identification of the measured gas. Gas discrimination is improved.

Preferably, the method comprises a step of determining the temperature $T_S$ of the sensitive layer from the determined thermal resistance $R_{th}$, the power P generated by the heating layer and a measurement of the ambient temperature $T_A$ according to the following formula:

$$T_S = P * R_{th} T_A$$

Preferably, the ambient temperature $T_A$ is measured by a temperature sensor external to the gas sensor.

Preferably, the method comprises a preliminary step of determining the thermal resistance $R_{th}$ of the heating layer by contacting the gas sensor with a predetermined standard gas. Thus, the determination of the temperature of the sensitive layer is optimal since the thermal resistance $R_{th}$ is determined individually for each gas sensor.

Preferably, the amplitude of thermal variation is at least 200° C., preferably at least 300° C. Preferably, the temperature variation range is between 100° C. and the maximum temperature accepted by the sensor, for example, in the order of 500° C. Such a temperature range makes it possible to reach temperatures where oxidation-reduction reactions occur.

Preferably, the thermal variation frequency $F_{th}$ is between 0.1 Hz and 1 Hz, that is a variation range from 1 second to 10 seconds.

The invention also relates to an assembly of a sensor for measuring a plurality of gases and a calculator for controlling said sensor, said sensor comprising a sensitive layer configured to measure said at least one gas having an impedance Zs and a heating layer on which the sensitive layer is mounted, said heating layer being configured to be supplied with electric energy in order to vary the temperature of the sensitive layer, said calculator being configured to implement the method as set forth above.

Preferably, the calculator comprises a memory zone comprising the database for implementing the method as set forth above.

BRIEF DESCRIPTION OF THE DRAWINGS

The invention will be better understood upon reading the following description, given only by way of example, and referring to the appended drawings in which.

It should be noted that the figures set out the invention in detail to implement the invention, said figures can of course be used to better define the invention if necessary.

DETAILED DESCRIPTION

Figure 1:
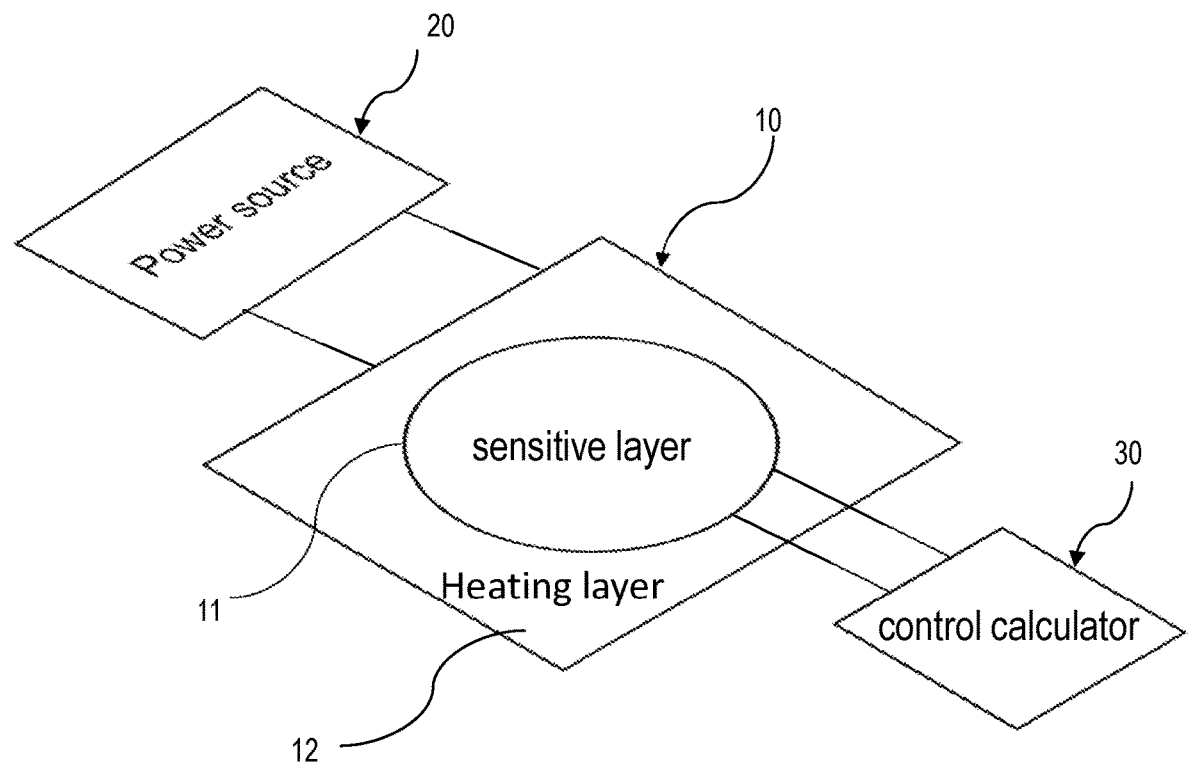
FIG. 1 is a schematic representation of one embodiment of a gas measurement sensor according to the invention.

With reference to FIG. 1, a gas measurement sensor 10 according to the invention is schematically represented. The measurement sensor 10 is supplied with energy by a power source 20 and a calculator 30 is configured to determine the amount of gas measured by the sensor 10.

The measurement sensor 10 is in the form of a metal-oxide sensor, also referred to as MOX. Such a sensor 10 comprises a layer 11 sensitive to at least one gas and a heating layer 12 on which said sensitive layer 11 is mounted.

The sensitive layer 11 is configured to react with a gas to detect its presence at the measurement sensor 10.

The sensitive layer 11 is in contact with the air and is adapted to absorb molecules of the gas to be measured. The absorption of these molecules varies the electrical conductivity across the sensitive layer 11, and thus the impedance ZS across the sensitive layer 11, by virtue of an oxidation-reduction reaction, thereby determining the amount of said gas present in the air in contact with the sensitive layer 11.

The sensitive layer 11 comprises an oxide enabling the oxidation-reduction reaction with the gas, for example, molecules of tin dioxide (SnO2), titanium dioxide (TiO2), tungsten trioxide (W03) and/or Niobium oxide (Ne2O5) with dopings of Platinum (Pt), Gold (Au), Germanium (Ge) and/or Palladium (Pd) elements. The chemical elements which are mixed with molecules allow the latter to be doped in order to optimize their function of absorbing molecules of the gas to be measured.

When molecules of the gas to be measured are absorbed by the sensitive layer 11, the impedance ZS across the same varies, which makes it possible to determine the presence as well as the amount of the gas to be measured. In other words, the amount of gas present in the air is measured from the variation in the impedance of the sensitive layer 11. To measure the variation in the impedance, the sensitive layer 11 is supplied with electric energy by the calculator 30 as will be described later. For this purpose, the sensitive layer 11 is electrically connected to the calculator 30.

The heating layer 12 is controlled in order to modify the temperature of the sensitive layer 11.

Such a modification in its temperature allows the sensitive layer 11 to absorb different gases depending on the temperature of the sensitive layer 11. In other words, each temperature of the sensitive layer 11 allows the amount of a gas to be measured. Thus, the measurement sensor 10 is configured to measure different gases by modifying the temperature of the sensitive layer 11. The heating layer 12 is supplied with electric energy in order to control the temperature as will be described later. For this purpose, the heating layer 12 is electrically connected to the power source 20.

By virtue of the heating layer 12, a single sensitive layer 11 allows different gases to be measured. This allows a single measurement sensor 10 to be used to measure the amount of several gases, thus limiting the electric power consumption and cost of such measurements.

The heating layer 12 in this example comprises a substrate, such as ceramic or silicon, and elements, such as gold, adapted to release heat when an electric current passed therethrough.

According to the invention, the temperature TS of the sensitive layer 11 is controlled by the heating layer 12 in order to enable accurate measurements of the sensitive layer 11. For this purpose, the temperature TS of the sensitive layer 11 is determined from the following equation:

$$T_S = P * R_{th} + T_A$$

where P is the power generated by the heating layer 12, Rth is the thermal resistance of the heating layer 12 to the sensitive layer 11 and TA is the ambient temperature.

In other words, the temperature TS of the sensitive layer 11 depends on the ambient temperature TA and the power P generated by the heating layer 12. The use of the thermal resistance Rth allows heat transfer losses between the heating layer 12 and the sensitive layer 11 to be taken into account.

The temperature TS of the sensitive layer 11 is thus accurately determined from the power P generated by the heating layer 12 from the electric energy supplied by the power source 20. As the temperature range over which the sensitive layer 11 measures a particular gas is reduced, the accurate determination of the temperature of the sensitive layer 11 allows the gas that is measured by the sensitive layer 11 to be accurately determined.

The ambient temperature TA is measured by a temperature sensor, thus providing an accurate measurement. Such a temperature sensor may be external to the measurement sensor 10 or included in the measurement sensor 10.

The thermal resistance Rth of the heating layer 12 corresponds to the heat loss between the heating layer 12 and the sensitive layer 11. The thermal resistance Rth is independent of the gas to which the measurement sensor 10 is subjected. Therefore it is determined prior to the measurements made by the measurement sensor 10. It can especially be determined upon designing the measurement sensor 10. If the thermal resistance Rth varies from one measurement sensor 10 to another, it can be determined for each measurement sensor 10 after its manufacture. For this purpose, each measurement sensor 10 is brought in the presence of a standard gas. Such a standard gas is a gas for which the behavior of the sensitive layer 11 is known. The heating layer 12 is then subjected to a theoretical curve of power P so that the sensitive layer 11 detects the standard gas. As the actual power at which the sensitive layer 11 detects the standard gas is known, the thermal resistance Rth is determined from the offset between the power of the theoretical curve at which the sensitive layer 1 detected the standard gas and the actual power. Following this calibration step, the thermal resistance Rth is stored in the calculator 30 in order to allow the sensitive layer 11 to be optimally controlled.

The power source 20 is configured to supply electric energy to the heating layer 12 so that the latter generates heat. As illustrated in FIG. 1, the power source 20 is electrically connected to the heating layer 12.

Figure 2:
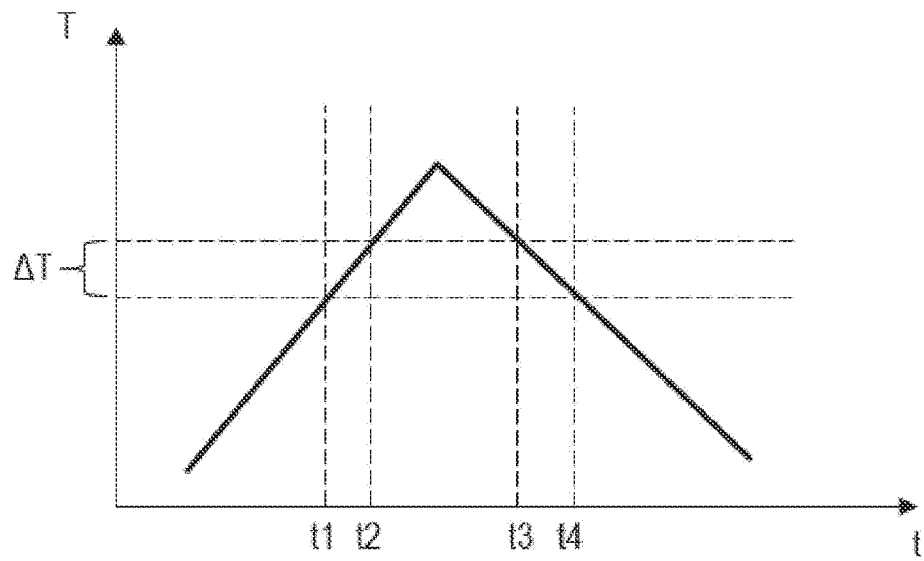
FIG. 2 is a schematic representation of a curve of variation in the temperature of the sensor of FIG. 1 over time.

According to the invention, the power source 20 is configured to supply energy to the heating layer 12 via a voltage ramp (not represented) comprising an increasing portion and a decreasing portion. The voltage of such a ramp thus varies linearly and slowly so that the temperature of the sensitive layer 11 also varies linearly and slowly forming a ramp as illustrated in FIG. 2. The temperature ramp thus allows a plurality of measurements to be made to detect different gases. To do this, the temperature ramp comprises a plurality of temperature ranges ΔT each corresponding to a gas to be measured. For the sake of clarity, a single temperature range ΔT has been illustrated in FIG. 2 corresponding to the measurement of a single gas. However, it goes without saying that the temperature ramp comprises as many temperature ranges ΔT as there are gases to be measured.

As illustrated in FIG. 2, the temperature ramp comprising an increasing portion and a decreasing portion, each temperature range ΔT is included in the increasing portion and in the decreasing portion. In other words, the temperature ramp passes through a temperature range ΔT when the temperature is increasing (between time instants t1 and t2) and when the temperature is decreasing (between time instants t3 and t4). This allows a same gas to be detected several times and at different time instants of the temperature ramp. This also makes it possible to easily identify the gases for which the behavior of the sensitive layer 11 differs depending on whether the temperature increases or decreases as will be described later. The presence of a rise and a fall thus forms a criterion for discriminating gases as will be set forth later.

The power source 20 is controlled by a calculator, which can be the control calculator 30.

The control calculator 30 is configured to determine the amount of a plurality of gases in the air.

As illustrated in FIG. 1, the control calculator 30 is electrically connected to the sensitive layer 11 in order to measure the impedance of the sensitive layer 11 and determine the presence of a gas therefrom. For this purpose, the calculator 30 supplies the sensitive layer 11 with electric energy. Preferably, the calculator 30 is configured to transmit a direct, periodic or pseudo-periodic voltage signal to the sensitive layer 11.

Figure 3:
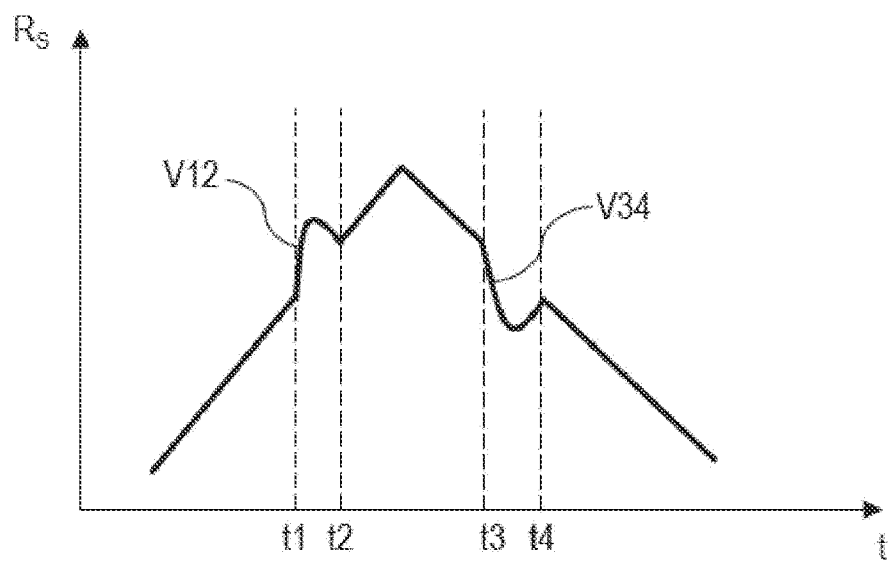
FIG. 3 is a schematic representation of a curve of variation in the impedance of the sensor of FIG. 1 when the temperature varies over time.

As illustrated in FIG. 3, the impedance Zs of the sensitive layer 11 varies with temperature. The impedance Zs follows a linear variation due to the linear variation in the temperature. In the presence of a determined gas, the impedance ZS of the sensitive layer 11 varies non-linearly, especially forming a peak as illustrated in FIG. 3, over a temperature range ΔT associated with the determined gas. Such a non-linear variation thus allows a gas to be detected and its amount to be measured. Advantageously, the variation in the impedance ZS over the temperature range ΔT can be, for some gases, different depending on whether the temperature is increasing or decreasing, in other words depending on whether the temperature ramp changes in an increasing or decreasing manner. This makes it possible to increase the reliability of detection of a gas.

The calculator 30 advantageously comprises a memory zone comprising a database comprising the different forms of variation in the impedance ZS of the sensitive layer 11 depending on the measured gas associated with the temperature Ts of the sensitive layer 11. This makes it possible to identify the gas detected by comparison between the variation in the impedance ZS measured and the variations recorded. Preferably, as will be set forth later, the database associates a predetermined gas with a temperature range Ts of the sensitive layer and with one or more variations in the impedance Zs, in particular, a rising variation and a falling variation. The database can be obtained empirically or from calculated data.

The impedance ZS is measured from the determination of the value of the voltage U across the sensitive layer 11. This voltage U can especially be determined using a voltage divider bridge in the case of a direct voltage signal generated by the calculator 30.

In the case of a periodic or pseudo-periodic voltage signal, especially of the chirp type, the sensitive layer 11 can then be assimilated to an RLC circuit, which makes it possible to calculate voltage U from the equation:

$$U = U_C + U_L + U_R \quad (1)$$

Where UC is the voltage across the capacitor C of the RLC circuit, UL is the voltage across the coil L of the RLC circuit and UR is the voltage across the resistor R of the RLC circuit.

Equation (1) can also be written as:

$$U = -\frac{j}{C\omega}I + jL\omega I + RI \quad (2)$$

With $\omega = 2\pi f$ where f is the frequency of the voltage signal.

When the frequency f of the signal is equal to the resonant frequency of the RLC system, equation (2) becomes:

$$I = Rf$$

Therefore, using the resonant frequency, it is easy to determine the resistance R of the RLC system which is equal to the impedance ZS of the sensitive layer 11. The resonant frequency of the RLC system can be determined by sweeping all frequencies and determining the frequency for which the value of current I is highest. Alternatively, the resonant frequency of the RLC system can be determined by sweeping all frequencies and determining the frequency for which phase shift between I and U is zero.

The use of such an RLC system is further advantageous because it allows the measurement, further to variations in the impedance ZS of the sensitive layer 11, of capacitive type variations, in other words of the capacitor C of the RLC system, and of the inductive type, in other words of the coil L. These different variations can then be used to determine the gas detected, the memory zone of the calculator 30 then comprising different forms of these variations depending on the gas measured and depending on the temperature of the sensitive layer.

Figure 4:
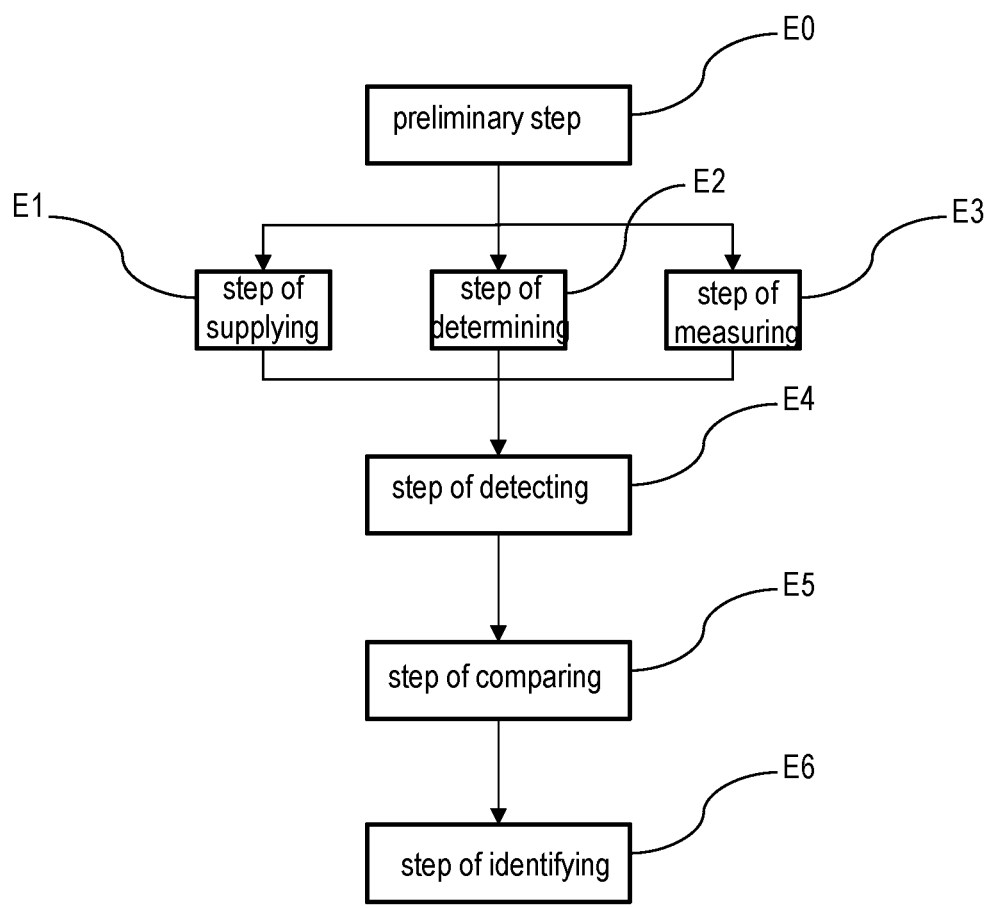
FIG. 4 is one exemplary implementation of a method for controlling a measurement sensor according to the invention.

An implementation of the method for controlling a measurement sensor 10 according to the invention will now be described with reference to FIGS. 2 to 4.

In a preliminary step E0, which can especially be carried out at the factory, the thermal resistance Rth of the heating layer 12 is determined. For this purpose, the measurement sensor 10 is brought in the presence of a standard gas for which the behavior of the measurement sensor 10 is known.

When using the measurement sensor 10, a voltage ramp is applied to the heating layer 12 in a step E1 in order to vary the temperature of the sensitive layer 11.

The temperature TS of the sensitive layer 11 is continuously determined, in a step E2, from the equation:

$$T_S = P \cdot R_{th} + T_A$$

where P is the power generated by the heating layer 12, Rth is the thermal resistance of the heating layer 12, and TA is the ambient temperature. The temperature TS then follows a ramp as illustrated in FIG. 2.

In a known manner, the power P generated by the heating layer 12 is a direct function of the voltage applied to the heating layer 12 and can be conveniently deduced.

The calculator 30 further measures, in a step E3, the impedance ZS of the sensitive layer 11 so as to generate a curve of variation in the impedance ZS as illustrated in FIG. 3.

In a step E4, with reference to FIG. 3, the calculator 30 detects two non-linear variations V12, V34 in the impedance Zs on the curve of variation. The calculator 30 then determines the time interval (between time instants t1 and t2, on the one hand, and between time instants t3 and t4, on the other hand as illustrated in FIG. 3) during which the variations V12, V34 have been detected. In this example, a convex variation V12 is detected between time instants t1 and t2 while a concave variation V34 is detected between time instants t3 and t4.

The calculator 30 then determines the temperature range ΔT corresponding to the time intervals determined from the temperature variation ramp.

In a step E5, the calculator 30 then compares the variations V12, V34 to the variations stored in the memory zone of the calculator 30 by correspondence of variation form and temperature range ΔT.

Finally, the calculator 30 identifies the detected gas from similarities in the comparison with recorded variations. In other words, the gas is identified as the one corresponding to the recorded variation the form of which is closest to the form of the detected variation. The gas measurement can thus be associated with a predetermined gas. The use of a variation in the rise and fall improves discrimination performance.

By virtue of the temperature variation, it is thus possible to detect different gases during this variation by virtue of the detection of non-linear variations in the impedance Zs of the sensitive layer 11. Each variation detected is separated from the others per temperature range in order to compare them to the variations present in the database and thus to detect the nature of the different gases measured. In other words, the smart control of a single gas sensor makes it possible to measure the amount of a plurality of different gases. Such a sensor is efficient while remaining economical.

The invention claimed is:

1. A method for detecting at least one amount of gas of at least one predetermined gas from a sensor for measuring a plurality of gases, said sensor comprising a sensitive layer configured to measure the plurality of gases having an impedance Zs and a heating layer on which the sensitive layer is mounted, said heating layer being configured to be supplied with electric energy in order to vary the temperature of the sensitive layer, said method comprising:
   a step of supplying the heating layer with at least one first increasing voltage ramp defining a linear variation in the supply voltage and then with a second decreasing voltage ramp defining a linear variation in the supply voltage between a low voltage value and a high voltage value in order to modify the temperature of the sensitive layer during a variation period according to a temperature ramp comprising an increasing portion and a decreasing portion, the temperature ramp comprising a plurality of temperature ranges ΔT each corresponding to a gas to be measured,
   a step of measuring:
   a first variation in the impedance Zs of the sensitive layer at a given temperature range ΔT of the sensitive layer during the first increasing ramp, and
   a second variation in the impedance Zs of the sensitive layer measured at the same given temperature range ΔT of the sensitive layer during the second decreasing ramp, the given temperature range ΔT corresponding to a given gas to be measured;
   a step of comparing, to a database, the first variation in the impedance Zs and the second variation in the impedance Zs in order to determine the amount of gas associated with said given gas.

2. The method according to claim 1, wherein the method comprises a step of determining the temperature $T_S$ of the sensitive layer from a thermal resistance $R_{th}$ determined, the power P generated by the heating layer and a measurement of the ambient temperature $T_A$ according to the following formula:

$$T_S = P*R_{th}T_A$$

3. The method according to claim 1, wherein the method comprises a preliminary step of determining a thermal resistance $R_{th}$ of the heating layer by contacting the gas sensor with a predetermined standard gas.

4. The method according to claim 1, wherein an amplitude of thermal variation is at least 400° C.

5. The method according to claim 1, wherein a frequency of thermal variation is between 0.1 Hz and 1 Hz.

6. An assembly of a sensor for measuring a plurality of gases and a calculator for controlling said sensor, said sensor comprising a sensitive layer configured to measure said at least one gas having an impedance Zs and a heating layer on which the sensitive layer is mounted, said heating layer being configured to be supplied with electric energy in order to vary the temperature of the sensitive layer, said calculator being configured to implement the method according to claim 1.

7. The assembly according to claim 6, wherein the calculator comprises a memory zone comprising the database.

* * * * *